United States Patent [19]

McGovern et al.

[11] Patent Number: 4,764,366
[45] Date of Patent: Aug. 16, 1988

[54] PERSISTENT ATTRACTANTS FOR THE MEDITERANEAN FRUIT FLY, THE METHOD OF PREPARATION AND METHOD OF USE

[75] Inventors: Terrence P. McGovern, Bowie, Md.; Roy T. Cunningham, Hilo, Hi.

[73] Assignee: The United States of America as represented by the Secretary of Agriculture, Washington, D.C.

[21] Appl. No.: 42,920

[22] Filed: Apr. 27, 1987

[51] Int. Cl.$^4$ .................. A01N 25/00; C07C 69/74; C07C 61/08; C07C 101/02
[52] U.S. Cl. .................................... 424/84; 560/125; 562/507
[58] Field of Search .................. 424/84; 560/125; 562/507

[56] References Cited

U.S. PATENT DOCUMENTS

| | | | |
|---|---|---|---|
| 2,851,392 | 9/1958 | Gertler | 424/84 |
| 3,016,329 | 1/1962 | Beroza et al. | 424/84 |
| 3,743,719 | 7/1973 | Beroza et al. | 424/84 |
| 4,152,422 | 5/1979 | Ohinata et al. | 424/84 |

OTHER PUBLICATIONS

Chemical & Engineering News, Apr. 15, 1957, pp. 80–81.
M. Beroza, N. Green, and S. I. Gertler, *Agricultural and Food Chemistry*, "New Attractants for the Mediterranean Fruit Fly", vol. 9, No. 5, pp. 361–365 (Sep. 1961).
S. I. Gertler, L. F. Steiner, W. C. Mitchell and W. F. Barthel, *Agricultural and Food Chemistry*, "Esters of 6-Methyl-3-Cyclohexene-1-Carboxylic Acid as Attractants for the Mediterranean Fruit Fly", vol. 6, No. 8, pp. 592–594 (Aug. 1958).

*Primary Examiner*—Shep K. Rose
*Assistant Examiner*—John M. Kilcoyne
*Attorney, Agent, or Firm*—M. Howard Silverstein; David G. McConnell; Beverly K. Johnson

[57] ABSTRACT

Novel lower alkyl esters of iodo-trans-2-methylcyclohexanecarboxylic acid are useful to attract the Mediterranean Fruit Fly, "Medfly," for prolonged periods of time. The esters are competitive in attraction with the current "standard" attractant, Trimedlure, but are much more persistent. The esters may be economically produced and possess the dual properties required for effective use in Medfly control programs.

12 Claims, No Drawings

PERSISTENT ATTRACTANTS FOR THE MEDITERANEAN FRUIT FLY, THE METHOD OF PREPARATION AND METHOD OF USE

BACKGROUND OF THE INVENTION

1. Field of the Invention

This invention relates to novel attractants for the Mediterranean Fruit Fly, *Ceratitis capitata* Wiedmann, commonly referred to as the "Medfly." More particularly, the present invention relates to novel aliphatic esters of iodo-trans-2-methylcyclohexanecarboxylic acid, the method of their preparation and the method of use thereof to attract the Medfly for prolonged periods of time.

2. Description of the Prior Art

Attacking over 250 varieties of fruits, nuts and vegetables, the Medfly is one of our most serious crop pests. Found predominately in Hawaii and Central America, the Medfly has periodically invaded the mainland of the United States causing major economic losses. Consequently, there exists a great need for effective programs to control this pest.

Several attractants for the Medfly are known. Siglure (1-methylpropyl trans-6-methyl-3-cyclohexenecarboxylate) was the first synthetic lure found to have significant attraction to the Medfly. Medlure (1-methylpropyl 4(and 5)-chloro-trans-2-methylcylohexane carboxylate) and trimedlure (1,1-dimethylethyl 4(and 5)-chloro-trans-2-methylcyclohexanecarboxylate), hereinafter referred to as "TML," were later reported to be greatly superior as Medfly attractants.

Currently, TML is the "standard" attractant most widely used in traps for survey and detection of the Medfly. TML evaporates rapidly during hot weather thereby necessitating frequent and costly rebaiting of the traps. Further, the short residual life of TML (as well as Medlure and Siglure) mitigates against the development of an economical male-annihilation formulation of attractant pluse insecticide. TML also forms crystals during cold-weather storage so that the amount of the attractant is reduced in the supernatant. Because these crystals do not readily redissolve, special storage problems can occur in large volume programs.

SUMMARY OF THE INVENTION

An object of this invention is to provide novel esters which are highly attractive to the Medfly for prolonged periods of time.

Another object of this invention is to provide persistent Medfly attractants which are comparable in attraction with TML but do not possess the deficiencies associated with TML.

We have accomplished the aforementioned objects by providing lower alkyl esters of iodo-trans-2-methylcyclohexanecarboxylic acid which when applied in effective amounts are highly attractive to the Medfly for prolonged periods of time. In addition to being much more persistent than TML, the esters of the invention are not prone to crystallization as is TML, and is more facilely and economically produced than TML.

DETAILED DESCRIPTION OF THE INVENTION

The compounds of the present invention are represented by the general formula

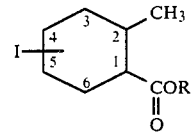

wherein —CH$_3$ and —COOR are in a trans-configuration and I is in both an equatorial and axial conformation and is located at either the 4 or 5 ring position; and wherein R is an aliphatic radical having from 1-5 carbon atoms and is selected from the group consisting of lower alkyls and fluoro-substituted lower alkyls.

It is within the scope of the invention to use mixtures of the 4- and 5-iodo isomers of the invention esters, said mixture being represented by the general formulae

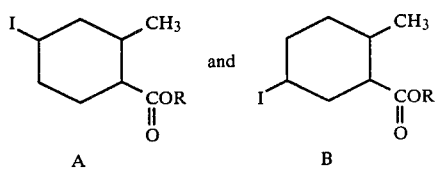

wherein —CH$_3$ and —COOR are in the trans-configuration and I is in both the equatorial and axial conformation; and wherein R is an aliphatic radical having from 1-5 carbon atoms and is selected from the group consisting of lower alkyls and fluoro-substituted lower alkyls, said R in each of formulae A and B being identical. In general, the mixtures within the compass of the invention consists of from about 35 to 75% of isomer A and 25 to 65% of isomer B. Preferably isomer A consists of from about 45 to 65% of the mixture and isomer B consists of 35 to 55% of the mixture.

Examples of esters in accordance with the invention are methyl 4(and 5)-iodo-trans-2-methylcyclohexanecarboxylate; ethyl 4(and 5)-iodo-trans-2-methylcyclohexanecarboxylate; 1-methylethyl 4(and 5)-iodo-trans-2-methylcyclohexanecarboxylate; 1-methylpropyl 4(and 5)-iodo-trans-2-methylcyclohexanecarboxylate; 2,2,2,-trifluoroethyl 4(and 5)-iodo-trans-2-methylcyclohexanecarboxylate; 2,2,3,3,3-pentafluoro 1-methylpropyl 4(and 5)-iodo-trans-2-methylcyclohexanecarboxylate; and 2,2,3,3,4,4,4-heptafluoro-1-methylbutyl 4(and 5)-iodo-trans-2 methylcyclohexanecarboxylate.

For purposes of the invention, the term "4 and 5" is used herein to designate a mixture of the 4- and 5-iodo isomers.

The esters of the present invention are prepared by either of two procedures. In one procedure, the corresponding trans-6-methyl-3-cyclohexenecarboxylic acid (as prepared by a Diels-Alder reaction) is heated in a pressure vessel for 3 to 6 hours at elevated temperatures, preferably not exceeding about 115° C., with aqueous hydriodic acid in the presence of an organic solvent, such as dioxane. The resultant iodo-trans-2-methylcyclohexanecarboxylic acid is a mixture of the 4- and 5-iodo isomers and is converted to the corresponding acid halide by reacting with a suitable halogenating agent, such as thionyl chloride, phosphorus trichloride or phosphorus tribromide, under mild conditions, preferably at room temperature. The acid halide is then reacted with the appropriate alcohol in a suitable solvent such as benzene or anhydrous ethyl ether in the presence of a hydrochloric acid scavenger, such as pyridine, to yield the ester of the invention.

A second procedure useful to prepare the esters of the invention employs an ester intermediate as the starting material. Under this preparation, the corresponding trans-6-methyl-3-cyclohexenecarboxylate (as prepared by a Diels-Alder reaction) is heated directly with aqueous hydriodic acid in a pressure vessel in the presence of an organic solvent, such as dioxane, at elevated temperatures, preferably not exceeding about 115° C., for 3 hours. An advantageous feature of this synthetic route over the abovementioned procedure resides in the fact that tert-butyl esters, such as TML, are extremely susceptible to cleavage even under mildly acidic conditions with the inhibition of isobutylene. Consequently, this single step procedure offers a quicker and a more economical production of the invention ester over that of TML.

In either of the two procedures, isolation of the ester is accomplished by sequentially washing the crude reaction mixture with dilute acid, dilute base and saturated salt solutions. The crude product is thereafter dried over a suitable drying agent, filtered and the solvent removed. Final purification is accomplished by fractional distillation under high vacuum.

Although the preparative procedures described above are the preferred synthesis for the compounds of the invention, it is within the scope of this invention to prepare the esters using any suitable esterification procedure. The iodo atoms of the invention esters are in both an equatorial and axial conformation, thus providing four stereoisomers for each ester. In order to optimize the attractiveness of the final product, the isomeric content of the ester can easily be varied by changing the reaction temperature during preparation of the esters.

The esters may be used as is or they may be dissolved in volatile inert solvents such as liquid hydrocarbons, emulsified in water, or admixed with any other solid or inert liquid carrier. When used in actual practice in the field, the compounds may be impregnated on a solid carrier such as paper, cloth, sawdust, wood chips, or other absorbent material. The attractants may also be dispersed into the atmosphere by spraying or by dipping wicks into containers holding the ester composition. Further, the attractants may be used in bait traps usually provided with means to prevent the exit of insects so that the size and location of infestations may be ascertained.

For optimum results, the esters of the invention should be used in a substantially pure form, that is, the esters must be free of undesirable contaminants that tend to mask or otherwise inhibit their effectiveness as an attractant. It is within the compass of the invention to use the esters either individually or in combination. The invention esters may also be used with other Medfly attractants or control agents, such as insecticides, chemosterilants or the like. When used, however, these agents should be used in an amount which, as readily determined by one skilled in the arts, will not interfere with the effectiveness of the invention esters.

The invention is further demonstrated by the following examples which are intended only to further illustrate the invention and not to limit the scope of the invention as defined by the claims.

EXAMPLE 1

The preparation of ethyl 4(and 5)-iodo-trans-2-methylcyclohexane carboxylate via the Diels-Alder acid adduct intermediate is hereinafter illustrated.

21 g of trans-6-methyl-3-cyclohexenecarboxylic acid (0.15 mole) were added to a pressure bottle along with 60 ml of 57% hydriodic acid and 30 ml of p-dioxane. The pressure bottle was equipped with a magnetic stirrer, securely capped, and placed in an oil bath held at 75° C. The reaction mixture was stirred vigorously while being held in the bath for 3 hours. After cooling, the reaction mixture was poured into water and the organic layer was taken up in ether. The ether layer was washed 2 times with water, then the organic acid was extracted from the crude reaction mixture with 10% aqueous sodium hydroxide. The alkaline portion was strongly acidified. The released organic acid was taken up in ether and was washed 3 times with water, then with dilute sodium bisulfite solution, again with water, dried over anhydrous magnesium sulfate and filtered. After removal of the solvent the crude iodo acid (ca 36 g) was used directly in the acid chloride synthesis. 26.8 g of the iodo acid (0.1 mole) was dissolved in 25 ml of benzene and 9 ml of thionyl chloride (0.125 mole) was added dropwise at room temperature. The reaction mixture was stirred overnight and the excess thionyl chloride and benzene were removed under vacuum with slight warning (40° C.). The crude acid chloride was added dropwise to an excess of ethanol (12 ml) and 8 ml of pyridine in anhydrous ether. After standing overnight, the reaction mixture was extracted sequentially with water, dilute aqueous hydrochloric acid and sodium hydroxide and finally with saturated salt solution. After drying over anhydrous magnesium sulfate, the crude product was isolated and purified by fractional distillation under high vacuum, b.p. 81° C./0.2 mm Hg, $n_D^{25}$ 1.5127, recovered yield 20.2 g, approximately 43% of which consisted of the 5-iodo ester and 57% of the 4-iodo ester. If the product darkens excessively after distillation, the excessive color can be removed by washing the product with dilute sodium bisulfite solution.

EXAMPLE 2

2,2,2-trifluoroethyl 4(and 5)-iodo-trans-2-methylcyclohexanecarboxylate was synthesized in a 0.02 mole reaction in accordance with the procedure described in Example 1, and purified by distillation under high vaccum, b.p. 65°-6° C./0.1 mm, $n_D^{25}$ 1.4718, recovered yield 3.55 g (about 47% 5-iodo ester and about 53% 4-iodo ester).

EXAMPLE 3

The preparation of ethyl 4(and 5)-iodo-trans-2-methylcyclohexane carboxylate via the Diels-Alder ester adduct is illustrated.

8.4 g of ethyl trans-6-methyl-3-cyclohexenecarboxylate, 20 ml of 57% hydriodic acid, and 10 ml of p-dioxane were placed in a pressure bottle in accordance with the procedure as described in Example 1. The compound was isolated by dissolving the crude reaction mixture in ether and washing with water to remove excess hydriodic acid. The ether layer was then extracted sequentially with 10% sodium hydroxide, dilute sodium bisulfite, and saturated salt solutions and dried over anhydrous magnesium sulfate. After filtration and removing the solvent the crude product was purified by fractional distillation under high vacuum, b.p. 81°-2° C./0.3 mm Hg, $n_D^{25}$ 1.5137, recovered yield 9.3 g (about 47% 5-iodo ester and about 53% 4-iodo ester).

EXAMPLE 4

To determine the effectiveness of the esters of the invention, a field test was conducted in a macadamia nut orchard at Keaau, Hawaii, from August 1986 to October 1986.

Medfly captures using ethyl and 2,2,2-trifluoroethyl 4(and 5)-iodo-trans-2-methylcyclohexanecarboxylate were compared with captures using TML at various dosages. Treatments were applied to cotton wicks (9.5 mm diam.×12.7 mm length; Johnson and Johnson No. 2) in standard Jackson sticky traps. Four dosages of each attractant in the amount of 80 µl, 40 µl, 20 µl, and 10 µl, were applied undiluted to each wick. Six replicates were used. At the 80 µl dosage, a freshly baited TML wick, in addition to the TML wick that was allowed to age along with the other attractants, was added to the test prior to each fly release. Sterile laboratory-reared medflies were released throughout the test plot in a uniform manner at 0, 1, 2, 3, 6, 7, 8, 9, 10, 14 and 15 days posttreatment. Fresh sticky inserts were placed in the traps prior to each release and remained in the trap throughout the test interval.

The TML used in the tests was obtained commercially from UOP in East Rutherford, N.J.

Data was analyzed by analysis of variance, and means were separated by Duncan's multiple range test at the P=0.05 level (Duncan 1951). The results are recorded in Table 1.

Table 1 clearly shows the high attraction and superior persistence of the invention esters. Freshly baited ethyl and trifluoroethyl esters of the invention were competitive in attraction with freshly baited samples of TML. When aged along with TML, the invention esters were notably more persistent than TML which lasted a mere 3 days at the maximum dosage. The ethyl ester of the invention is shown to be by far the most persistent of the lures tested. After 15 days, the ethyl ester maintained a high medfly catch at the 80 µl dosage which compared favorably to a freshly baited TML wick. Even at the lower 10 µl dose, the ethyl ester outlasted the maximum 80 µl dose of the aged TML.

EXAMPLE 5

A field test similar to that described in Example 3 was conducted in a macadamia nut orchard at Keaau, Hawaii from September 1986 to October 1986.

Medfly captures using the ethyl esters of 4(and 5)-fluoro-, 4(and 5)-chloro-, and 4(and 5)-bromo-trans-2-methylcyclohexanecarboxylates (each synthesized from the corresponding halo acid via the method of esterification as described in Example 1) were compared to those captures using the ethyl iodo ester of the invention and TML (same as described in Example 4).

The bioassay was the same as described in Example 4 except that the lures were applied in a 0.1 ml dosage and medflies were released at 0, 1, 2, 3, 6, 8, 10, 13, 15, 17, 20, 22, and 24 days posttreatment.

Data were analyzed in accordance with Example 4. The results are reported in Table 2.

The chlorinated ester was more attractive than the brominated ester, but not significantly so, before it began to fail. Both were substantially less attractive than TML. Unexpectedly however, the invention ester not only surpassed the attraction of its fluoro-, chloro- and bromo-analogs but lasted a minimum of 2 times longer than TML while maintaining medfly catches that were not significantly different from those obtained using fresh TML. In addition, the iodo derivative does not rapidly lose effectiveness as it begins to fail because of evaporation as

TABLE I

Medfly captures[a] by ethyl and 2,2,2-trifluoroethyl 4(and 5)-iodo-trans-2-methylcyclohexanecarboxylate when compared with trimedlure (TML) at various dosages.

| Dose | Ester | Days aged | | | | | | | |
|---|---|---|---|---|---|---|---|---|---|
| | | 2 | 3 | 6 | 7 | 8 | 9 | 10 | 15 |
| 80 µl | TML (fresh) | 1310ab | 1597ab | 1216ab | 1026ab | 1534a | 1446a | 1635a | 942a |
| | TML (aged) | 1271ab | 1306abcd | 6cd | 1d | 0e | 0c | 0d | 0c |
| | Ethyl | 1184ab | 1250abc | 1135ab | 1329a | 1473a | 1515a | 1165b | 637b |
| | Trifluoroethyl | 1343a | 1966a | 1432a | 963ab | 441c | 50c | 7d | 0c |
| 40 µl | TML (aged) | 1116ab | 730de | 51e | 0d | 0e | 0c | 0d | 0c |
| | Ethyl | 830ab | 1086bcd | 814bc | 865b | 894b | 491b | 494c | 0c |
| | Trifluoroethyl | 1520a | 1853a | 1154ab | 2d | 2e | 0c | 0d | 0c |
| 20 µl | TML (aged) | 793b | 0f | 0e | 76d | 0e | 0c | 0d | 0c |
| | Ethyl | 1009ab | 1461ab | 898abc | 306c | 248d | 40c | 0d | 0c |
| | Trifluoroethyl | 1119ab | 1131bcd | 429d | 0d | 0e | 0c | 0d | 0c |
| 10 µl | TML (aged) | 215c | 0f | 0e | 0d | 0e | 0c | 0d | 0c |
| | Ethyl | 851ab | 701cde | 611cd | 31d | 0e | 0c | 0d | 0c |
| | Trifluoroethyl | 1015ab | 446e | 53e | 0d | 0e | 0c | 0d | 0c |

Catches followed by the same letter within a column are not significantly different at the 5% level (Duncan's multiple range test).
[a]Total capture from 6 replicates.

TABLE II

Medfly captures[a] by ethyl esters of 4(and 5)-halo-trans-2-methylcyclohexanecarboxylic acid when compared with trimedlure (TML).

| Ester | 4(and 5)- halo | Days aged | | | | | | | | | | | |
|---|---|---|---|---|---|---|---|---|---|---|---|---|---|
| | | 0 | 1 | 2 | 3 | 6 | 8 | 10 | 13 | 15 | 17 | 20 | 22 | 24 |
| TML (fresh) | | 1820a | 1239a | 1313ab | 1302ab | 911a | 1895a | 999a | 1018a | 970a | 1179a | 1921a | 1745a | 947a |
| TML (aged) | | 2048a | 1049a | 1376ab | 1337ab | 891a | 141b | 0b | 0b | 0b | 0c | 0c | 0c | 0c |
| Ethyl | F | 935b | 111b | 0c | 0c | 0c | 0c | 0b | 0b | 0b | 0c | 0c | 0c | 0c |

TABLE II-continued

Medfly captures[a] by ethyl esters of 4(and 5)-halo-trans-2-methylcyclohexanecarboxylic acid when compared with trimedlure (TML).

| Ester | 4(and 5)-halo | Days aged | | | | | | | | | | | | |
|---|---|---|---|---|---|---|---|---|---|---|---|---|---|---|
| | | 0 | 1 | 2 | 3 | 6 | 8 | 10 | 13 | 15 | 17 | 20 | 22 | 24 |
| Ethyl | Cl | 1469ab | 979a | 1060ab | 777b | 76c | 0c | 4b | 0b | 0b | 0c | 0c | 0c | 0c |
| Ethyl | Br | 1319ab | 794a | 988b | 841b | 337b | 3c | 0b | 0b | 0b | 0c | 0c | 0c | 0c |
| Ethyl | I | 2093a | 1203a | 1438ab | 1405a | 779a | 1394a | 848a | 913a | 1116a | 902b | 1166b | 861b | 392b |

Catches followed by the same letter within a column are not significantly different at the 5% level (Duncan's multiple range test).
[a]Total capture from 6 replicates. Initial dosage, 0.1 ml.

does TML and the other lures on Table 2. Nine days after it was last statistically equivalent with a freshly baited wick (15 days of aging), the iodo derivative was still catching large numbers of medflies when the test was terminated.

It is understood that modifications and variations may be made to the foregoing disclosure without departing from the spirit and scope of the invention.

We claim:

1. An attractant useful to attract the Mediterranean Fruit Fly for prolonged periods of time wherein said attractant comprises an isomeric mixture of compounds having the formulae

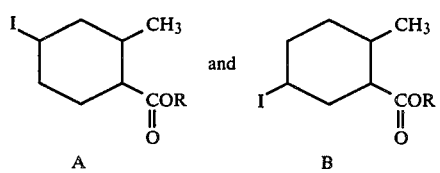

wherein A consists of from 35% to 75% of the mixture and B consists of from 25% to 65% of the mixture; wherein —CH₃ and —COOR are in the trans-configuration and —I is in both the equatorial and axial conformation; and wherein R is an aliphatic radical selected from the group consisting of ethyl and 2,2,2-trifluoroethyl, said R in each of formulae A and B being identical.

2. The attractant of claim 1 wherein R is ethyl.

3. The attractant of claim 2 wherein R is 2,2,2-trifluoroethyl.

4. The attractant of claim 1 wherein A consists of from 45% to 65% of the mixture and B consists of from 35% to 55% of the mixture.

5. The attractant of claim 1 wherein said attractants further comprise a Mediterranean Fruit Fly control agent.

6. The attractant of claim 5 wherein the Mediterranean Fruit Fly control agent is an insecticide.

7. A method of attracting the Meditteranean Fruit Fly for prolonged periods of time comprising subjecting the Mediterranean Fruit Fly for an extended period of time to an isomeric mixture of compounds having the general formulae

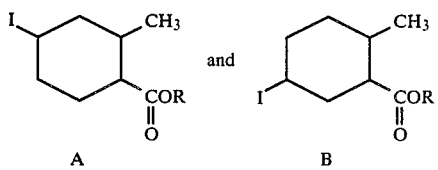

wherein —CH₃ and —COOR are in the trans-configuration and —I is in both the equatorial and axial conformation; wherein A consists of from 35% to 75% of the mixture and B consists of from 25% to 65% of the mixture; and wherein R is an aliphatic radical selected from the group consisting of ethyl and 2,2,2-trifluoroethyl, said R in each of formulae A and B being identical, in an amount effective to attract the Meditteranean Fruit Fly.

8. The method of claim 7 wherein R is ethyl.

9. The method of claim 7 wherein R is 2,2,2-trifluoroethyl.

10. The method of claim 7 wherein A consists of from 45% to 65% of the mixture and B consists of from 35% to 55% of the mixture.

11. The method of claim 7 wherein the composition further comprises a Mediterranean Fruit Fly control agent.

12. The method of claim 11 wherein the Mediterranean Fruit Fly control agent is an insecticide.

* * * * *